US005639461A

United States Patent [19]
Zakay-Rones et al.

[11] Patent Number: 5,639,461
[45] Date of Patent: Jun. 17, 1997

[54] INFLUENZA MACHINE

[75] Inventors: Zichria Zakay-Rones; Reuven Levy, both of Jerusalem, Israel

[73] Assignee: Yissum Research Development Company of the Hebrew University of Jerusalem, Jerusalem, Israel

[21] Appl. No.: 661,667

[22] Filed: Jun. 11, 1996

Related U.S. Application Data

[63] Continuation of Ser. No. 316,212, Sep. 30, 1994, abandoned.

[51] Int. Cl.$^6$ .................................................. A61K 39/145
[52] U.S. Cl. ................................................................ 424/209.1
[58] Field of Search ............................ 424/209.1, 210.1

[56] References Cited

U.S. PATENT DOCUMENTS

| | | | |
|---|---|---|---|
| 3,060,094 | 10/1962 | Dutcher et al. | 435/5 |
| 3,655,871 | 4/1972 | Werner et al. | 424/209.1 |
| 3,699,222 | 10/1972 | Isaacs et al. | 424/85.4 |
| 4,071,619 | 1/1978 | Peradze et al. | 424/209.1 |

FOREIGN PATENT DOCUMENTS

| | | |
|---|---|---|
| 268868 | 6/1989 | German Dem. Rep. . |

OTHER PUBLICATIONS

Hosaka et al., Virus Research (1985), vol. 0 (Suppl. 1): p. 56.

Lelie et al., J. of Medical Virology (1987), vol. 23: pp. 297–301.

Kilbourne, in Vaccines (Plokkin et al., eds.), W.B. Saunders Co., Philadelphia, 1988, pp. 420–434.

Barrett et al., in Methods of Immunological Analysis (Masseyeff et al., eds.) VCH Verlagsgesellschaft mbH, Weinheim, Dec. 22, 1992, vol. 2: pp. 116–132.

Goldstein et al, Applied Microbiology, Feb., 1970, vol. 19 (2): pp. 290–294.

Knight et al, The Journal of Experimental Medicine, Mar. 1, 1944, vol. 79(3): pp. 291–300.

*Primary Examiner*—Mindy Fleisher
*Assistant Examiner*—Terry A. McKelvey
*Attorney, Agent, or Firm*—Steinberg, Raskin & Davidson, P.C.

[57] ABSTRACT

The invention provides an influenza vaccine which comprises a heat inactivated whole virus influenza free of formalin and β-propiolactone (BPL).

12 Claims, No Drawings

INFLUENZA MACHINE

This is a continuation, of application Ser. No. 08/316,212, filed Sep. 30, 1994, now abandoned, which is incorporated by reference herein in its entirety.

BACKGROUND OF THE INVENTION

The present invention relates to an influenza vaccine.

More particularly the present invention relates to an inactivated whole virus influenza vaccine and to a method for the preparation thereof.

Influenza virus infection still continues to be an annual threat all over the world. The infection may be asymptomatic or may range from a mild upper respiratory infection to a severe disease complicated by pneumonia that may result in mortality. Although severe disease is more frequent in the very young, the chronically ill and the aged, the economic burden of the disease, even when mild, is enormous in the total number of working days lost.

The preferred strategy to control the disease is still annual routine immunization. For over twenty years it has been recommended that killed influenza vaccine be given annually to all persons with high risk conditions. The guiding principle behind the recommendation has been to reduce the mortality of epidemic influenza, morbidity and to prevent complications.

Inactivated virus vaccines are still today the primary tool used for inoculation against influenza.

Vaccines which are at present employed are whole virion inactivated vaccines wherein inactivation has been effected by using formalin or β-propiolactone (BPL). Also subunit or split vaccines are used for intramuscular (i.m) or subcutaneous (s.c.) immunization.

Live attenuated (i.e. temperature sensitive mutants) are suggested for intranasal (i.n.) application by instillation, aerosol or spray. Most of these vaccines, however, are still only experimental.

The routinely used vaccines purified on sucrose gradient by continuous flow centrifugation, are mostly inactivated by formol, and are whole virions, split or subunit (the latter being aimed especially for children), administered i.m. or s.c. by injection. The efficacy of the vaccines are mostly assessed by seroconversion or by x4 fold rise of humoral antibodies, mainly the hemagglutination inhibition antibodies.

The hemagglutinin of influenza virus is the major surface glycoprotein against which neutralizing antibodies are elicited, however, the isolated glycoproteins obtained by various methods (subunits, genetic engineered or synthetic) is antigenically inferior to whole virus, in producing humoral antibody response and an adjuvant might therefore be required. Moreover, the isolated antigen is not suitable for cases where IgA is the major protective antibody, as is the case in the respiratory tract.

In respiratory tract infections, antibodies of the secretory IgA type have a major role in the defence vs. infection as it neutralizes the virus at its entrance site.

The inactivated vaccines (whole or subunit) are incapable of inducing local antibody production at all or only in negligible level. At the most, a subunit vaccine of the virus can trigger a secondary response and only when it follows a first dose of active virus and not inactive, or subunit. Satisfactory local immunization is therefore not yet available as it is mostly attributed to the presence of live antigen and adequate and safe live vaccines are not yet available.

Beside humoral antibodies, cellular immune response (CMI) is also elicited. In that respect whole virus vaccines are also important. Recently more and more data has been gathered about the importance of CMI in the protection against infection with influenza virus. Cellular immunity is important in that it exhibits cross reactivity among the different strains within the A group, in contrast to the strain specificity of the antibody response. This phenomenon is dependent on the presence of several viral proteins such as the matrix and nucleoprotein. These proteins were conserved during decades as compared to the annual changes in the surface glycoproteins (hemmagglutinin and neuraminadase), which are mainly responsible for the antibody production.

There is great controversy over the safety and efficacy of the current killed vaccine. The use of BPL which was used in the past for inactivation is now prohibited due to its carcinogenicity. Formalin which is still widely used, is responsible for part of the side effects, and recently some doubts as to its safety were raised.

SUMMARY OF THE INVENTION

With this state of the art in mind, the present invention provides an influenza vaccine comprising a formalin-and β-propiolactone (BPL) free, heat-inactivated, whole virus influenza.

The invention also provides a process for inactivating whole virus influenza comprising heating harvested allantoic fluid containing influenza virus at a temperature of about 45°–59° C. for about 25–180 minutes whereby there is produced a formalin-and BPL-free, heat-inactivated, influenza whole virus, said virus being at least 99% inactivated.

In a preferred embodiment of the present invention said virus is combined with a non-carcinogenic inactivating agent to supplement said heat inactivation to inactivate all residual virus.

Preferably said inactivating agent is thimerosal in combination with ethyl ether. Thimerosal can be combined with the virus while it is subjected to heat inactivation or thereafter.

DETAILED DESCRIPTION

The inactivation procedure of the present invention, eliminates inactivation which is dependent on the use of biohazard chemicals. Such chemicals as BPL and/or formalin reduce safety of the vaccine and might be also reactogenic. Therefore, the inactive vaccine of the present invention, highly purified by a modified zonal purification procedure is safer, since BPL, formalin or any other carcinogenic chemical is not used. Moreover, the inactivated vaccine of the present invention evokes humoral antibodies following i.m. or i.p. injection to mice, similar to formalin inactivated vaccine, injected by the same route. What is more important—contrary to other inactive antigens, heat inactivated vaccine is still capable of evoking local antibody response against the surface glycoproteins. Also humoral antibodies are elicited in high protective levels. which persist for long periods. The heat inactivated antigen can also induce interferon in low levels. Interferon was not induced by formalin treated antigen.

The present vaccine is safer and more efficient and, being an inactive zonal purified whole virus vaccine, it can substitute for the routinely used vaccine for intramuscular and subcutaneous application, and also be used as a new vaccine for local intranasal application. This is an important step forward in the efforts to improve influenza vaccines. This vaccine would greatly enlarge the groups for targeting killed vaccine.

The purification procedure results in a vaccine containing a low concentration of protein, which minimizes to almost zero, adverse side effects.

The present method for the inactivation of influenza viruses is of great importance, as BPL previously used is banned from further use due to its carcinogenicity. Formalin which is still widely used has lately elicited doubts as to its safety.

The mode of inactivation is therefore of great advantage, as compared to the routinely inactivated vaccines which are in use.

The vaccine can substitute the routinely used formol inactivated vaccine injected i.m. or s.c. with similar level of humoral antibodies being produced.

The vaccine can be applied intranasally. Using this route of application, similar protective level of humoral antibodies are elicited, as well as local antibodies.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

DETAILED DESCRIPTION OF THE PREFERRED EMBODIMENTS

EXAMPLES

Preparation and Purification of Whole Virion Inactive Influenza Vaccine

Allantoic fluids from infected embryonated eggs (10–12 days old), 40–60 hr past infection is harvested following overnight refrigeration or 45 min at −20° C. and subjected to concentration and purification.

Clarified harvested allantoic fluid was subjected to heat inactivation at a temperature of about 55°–56° for 30 minutes in a water bath. Inactivation was carried out in the presence of merthiolate (Thiomersal) 1:20,000 final concentration or without. Following inactivation the antigen was purified and the purified antigen was suspended in buffer pH 7.2–4. Final antigen containing 6–7% sucrose, thiomersal 0.01% and ether 1%–2%. The residual virus is inactivated by the thiomersal and ether as tested in embryonated eggs.

| The final product: | 60–80 ug protein |
| | 5–6% sucrose |
| | $PO_4$ 0.1μ 0.15 NaCl pH 7.8–7.9 |
| | $10^{-3}$ μ EDTA |
| | 0.01% Thiomersal |
| | 0.05% Tween 80 |
| | 0.01%–0.02% ether |

The following influenza strains were heat inactivated
A/Taiwan/86 (NIB-16) ($H_1N_1$)
A/PRB/34 ($H_1N_1$)
A/Leningrad 360/86 ($H_3N_2$)
B/Ann Arbor A/Taiwan/1/86 ($H_1H_1$) was chosen since it is a recent strain in the current vaccine.

A/PR8/34 ($H_1N_1$) strain was chosen since it serves as a parental strain in many recombinants designated for vaccine preparation and the strain is pathogenic to mice, and therefore challenge experiments can be performed in the immunized animals. A/Leningrad 360/86 was chosen as a representative of A/$H_3N_2$ strain and B/Ann Arbor was chosen as a representative of a BN strain type of virus.

TABLE 1

Infectivity Inactivation Following Heat Treatment
Allantoic fluid (following clarification)

| Strain/ Treatment | none | 55–56° 30' | 55–56°–30' +1/20000 Thiomersal | 45°–3h. | 59° 30' |
|---|---|---|---|---|---|
| A/Taiwan 1/86 | $10^{8.5}$ | $10^{4.5}$ | n.d. | $10^{5.0}$ | n.d. (not done) |
| ($H_1N_1$) | $10^{8.5}$ | $10^{3.7}$ | n.d. | | n.d. |
| A/PR8/34 | $10^{9.0}$ | $10^{2.0}$ | $10^{1.0}$ | n.d. | n.d. |
| ($H_1N_1$) | $10^{8.0}$ | $10^{3.5}$ | $10^{2.8}$ | | |
| | $10^{8.5}$ | $10^{3.5}$ | $10^{3.0}$ | | $10^{1.24}$ |
| B/Ann Arbor | $10^{9.5}$ | $10^{4.5}$ | n.d. | n.d. | n.d. |
| A/Leningrad (H3N2) 360/86 | $10^{7.5}$ | $10^{2.5}$ | n.d. | n.d. | n.d. | a. Infectivity measured by titration in allantoic sac of embryonated eggs and determined as EID50/0.2 ml.

From Table 1 it can be seen that with all four representative strains heating at 55°–56° C. for 30 minutes resulted in over 99% decrease in infectivity.

Addition of Thiomersal during heat inactivation further decreased the infectivity of the tested $APR_8$ strain, Heating at 45° C. for 3 hours and at 59° C. for 30 minutes were also effective for decreasing infectivity by over 99%.

In Table 2 hereinafter it can be seen that the inactivation according to the present invention does not cause deterioration of hemagglutination activity of the virus thus assuring that the use of the inactivated virus will nevertheless result in the formation of the desired immunity including the formation of antibodies.

It is to be noted that even the decrease in activity resulting from heating at 59° C. for 30 minutes is not considered significant in the context of the test done.

TABLE 2

| Effect of Heat on Hemagglutination Titer of Allantoic Fluid | | | | |
|---|---|---|---|---|
| Strain/ Treatment | none | 55–56° 30' | 55–56°–30' +1/20000 Thiomersal | 45°–3h. | 59° 30' |
| A/Taiwan 1/86 | 1000–2000 | 1000–2000 | n.d. | 1000 | |
| ($H_1N_1$) | 2000–4000 | 2000–4000 | n.d. | n.d. | |
| A/PR8/34 | 1024 | 1024 | n.d. | n.d. | |
| ($H_1N_1$) | 2000 | 2000 | 2000 | | |

TABLE 2-continued

Effect of Heat on Hemagglutination Titer of Allantoic Fluid

| Strain/ Treatment | none | 55–56° 30' | 55–56°-30' +1/20000 Thiomersal | 45°-3h. | 59° 30' |
|---|---|---|---|---|---|
| | 1024 | 1024 | 1024 | n.d. | 512 |
| B/Ann Arbor | 1024 | 1024 | | | |
| A/Leningrad (H3N2) 360/86 | 1000 | 512–1000 | | | |

The purified suspensions of two of the above viral strains (2 batches of each) were further purified and were found inactive and sterile in bacteriological tests and were tested for the immunogenicity.

TABLE 3

Inactivity of concentrated purified material

| Strain/Treatment | | Thiomersal and Ether |
|---|---|---|
| A/Taiwan 1/86 | $10^{4.2}$ | negative |
| ($H_1N_1$) | $10^{3.5}$ | negative |
| A/PR8/34 | $10^{4.0}$ | negative |
| ($H_1N_1$) | $10^{3.7}$ | negative |

As can be seen from Table 3, residual infectivity in allantoic fluid was completely diminished in the purified concentrated virus suspension by further treatment with Thiomersal 1:10000 final concentration and ether 1–2%.

II. Immunological Studies

Mice were immunized interaperitoneally (i.p.) (0.5 ml) or i.n. 005–0.1 ml. At several time intervals titers of hemagglutination inhibition HI antibodies were tested.

In accordance with accepted protocol vaccine according to the invention was evaluated 21 days following mice immunization either j.p. or i.n.

The results are tabulated in Table 4 from which it can be seen that substantially 100% of the mice tested responded with high protective levels of humoral antibodies.

As shown in Table 5 antibodies were still present two months following immunization with protective levels of humoral antibodies still being in the range and magnitude recognized as affording protection.

TABLE 4

Humoral hemagglutination inhibition antibodies (HI) 21 days following immunization of mice with heat inactivated vaccines

| Strain | route of vaccination | vaccine dilution | no of mice responding | HI antibodies* |
|---|---|---|---|---|
| A/Taiwan 1/86 ($H_1N_1$) | i.p. | 1:10 | 9/9 | 380 |
| | i.p. | 1:10 | 9/9 | 100 |
| | i.n. | 1:5* | 7/7 | 60 |
| A/PR8/34 ($H_1N_1$) | i.p. | 1:25 | 7/8 | 365 |
| | i.n. | 1:5 | 14/14 | 240 |
| | i.m. | 1:5 | 10/10 | 160 |

*Average reciprocal titer of hemagglutination inhibitions antibodies. Each mice was tested individually.

TABLE 5

Persistence of humoral antibodies two months following immunization with heated A/PR$_8$/34

| Route of Vaccination | No. of mice responding | HI antibodies* |
|---|---|---|
| i.p. | 14/16 | 28.4 |
| i.n. | 9/14 | 30.0 |
| i.n. × 2[b] | 4/4 | 91.0 |
| i.n.[c] | 9/9 | 55.5 |

*Average of reciprocal of HI antibody titer.
[b]Mice were immunized twice with 12 days interval between immunization.
[c]Mice were innoculated with live virus, for control purposes.

COMPARATIVE EXAMPLE A

A/PR$_8$/34 strain vaccine was prepared according to the present method of inactivation and a similar vaccine was prepared using state of the art inactivation with formalin.

The two vaccines were then administered intranasally to two different groups of mice and the mice were tested individually 10 and 20 days after immunization.

As can be seen in the results tabulated in Table 6, humerol antibody response was significantly higher with the vaccine inactivated according to the present invention and only with the present vaccine was local antibody response elicited also in the lungs.

TABLE 6

Humoral and local antibodies following intranasal immunization with A/PR8/34

| | heated | | formol | |
|---|---|---|---|---|
| Vaccine day | humoral | local in lungs | humoral | local in lung |
| 10 | 160 | 16 | 40 | negative |
| 20 | 160 | 32 | 40 | negative |

COMPARATIVE EXAMPLE B

Mice were immunized with vaccine inactivated according to the present invention which vaccine was administered intranasally. A second group of mice which were not immunized were kept as controls. Mice were challenged 21 days following immunization and the results of said challenge experiments on the immunized and controlled mice are set forth in Table 7. As will be noted, in the first group experiment of the mice vaccinated none were found to be sick or dead while 75% of the control mice were found to be sick and 25% were found to be dead. In the second group of experiments one out of the fourteen mice immunized was found to be dead while 21 out of 29 of the control mice were found to be dead.

TABLE 7

Challenge experiments following intranasal immunization with heated A/PR8/34

| Vaccine | No. of mice | sick | dead |
|---|---|---|---|
| 7a A/PR8 | 8 | 0 | 0 |
| Control | 8 | 6/8 (75%) | 2/8 (25%) |
| 7b A/PR8 | 14 | 0 | 1/14 (7%) |
| Control | 29 | 0 | 21/29 (72.4%) |

TABLE 8

Immunization of mice with 3 months old vaccine (A/PR8)
(Shelf-life test)

| Route of Immunization | Antigen Dilution | Number of mice Responding | HI titer* |
|---|---|---|---|
| i.p. | 1:10 | 9/10 | 180 |
| i.p. | 1:25 | 8/9 | 240 |
| i.n. | 1:5 | 10/10 | 68 |

*Average of reciprocal of HI titer.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An influenza vaccine comprising whole influenza viruses that have been at least 99% inactivated by heat in conjunction with thimerosal as a non-carcinogenic influenza virus inactivating agent, said influenza vaccine further comprising thimerosal, and being free of formalin and β-propiolactone, said influenza vaccine effective to evoke both a protective humoral and a protective local antibody response.

2. The vaccine according to claim 1 further comprising ethyl ether.

3. The vaccine according to claim 1 prepared in a formulation suitable for intranasal administration thereof.

4. The vaccine according to claim 1 wherein said inactivation by heat comprises heating harvested allantoic fluid containing whole influenza viruses at a temperature ranging from about 45° C. to about 59° C. for about 25 to 80 minutes.

5. The influenza vaccine of claim 1 wherein said vaccine evokes production of hemagglutination inhibiting antibodies.

6. A process for producing an inactivated whole influenza virus vaccine comprising heating harvested allantoic fluid containing whole influenza viruses at a temperature ranging from about 45° C. to about 59° C. for about 25 to about 180 minutes to substantially heat inactivate said whole influenza viruses and combining said whole influenza viruses with thimerosal as a non-carcinogenic influenza virus inactiveting agent thereby producing a formalin and β-propiolactone free whole influenza virus vaccine at least 99% inactivated by heat and thimerosal, said influenza vaccine effective to evoke both a protective humoral and a protective local antibody response.

7. The process according to claim 6 wherein said inactivating agent further comprises ethyl ether.

8. A method for influenza vaccination comprising administering intranasally an influenza vaccine comprising whale influenza viruses that have been at least 99% inactivated by heat in conjunction with thimerosal as a non-carcinogenic influenza virus inactivating agent, said influenza vaccine further comprising thimerosal, being free of formalin and β-propiolactone, said influenza vaccine effective to evoke both a protective humoral and a protective local antibody response.

9. The method for influenza vaccination according to claim 8 wherein said vaccine is administered intranasally by spray.

10. The method for influenza vaccination according to claim 8 wherein said vaccine is administered intranasally by drops.

11. A method for influenza vaccination comprising administering intramuscularly an influenza vaccine comprising whole influenza viruses that have been at least 99% inactivated by heat in conjunction with thimerosal as a non-carcinogenic influenza virus inactivating agent, said influenza vaccine further comprising thimerosal, and being free of formalin and β-propiolactone, said influenza vaccine effective to evoke a protective humoral antibody response.

12. A method for influenza vaccination comprising administering subcutaneously an influenza vaccine comprising whole influenza viruses that have been at least 99% inactivated by heat in conjunction with thimerosal as a non-carcinogenic influenza virus inactivating agent said influenza vaccine further comprising thimerosal, and being free of formalin and β-propiolactone, said influenza vaccine effective to evoke a protective humoral antibody response.

\* \* \* \* \*

UNITED STATES PATENT AND TRADEMARK OFFICE
CERTIFICATE OF CORRECTION

PATENT NO. : 5,639,461
DATED : June 17, 1997
INVENTOR(S) : Z. Zakay-Rones, et al.

It is certified that error appears in the above-identified patent and that said Letters Patent is hereby corrected as shown below:

On the cover page, at item [54], delete "MACHINE" and replace with --VACCINE--.

At column 1, line 2, delete "MACHINE" and replace with --VACCINE--.

Signed and Sealed this

Twenty-third Day of September, 1997

Attest:

BRUCE LEHMAN

Attesting Officer

Commissioner of Patents and Trademarks